United States Patent [19]

Yarrington

[11] Patent Number: 4,847,276

[45] Date of Patent: Jul. 11, 1989

[54] TREATMENT OF THROMOBOCYTOSIS WITH 5-(4-CHLOROPHENYL)-2,4-DIEMTHYL-3H-1,2,4-TRIAZOLE-3-THIONE

[75] Inventor: John T. Yarrington, Worthington, Ohio

[73] Assignee: Merrell Dow Pharmaceuticals Inc.

[21] Appl. No.: 241,160

[22] Filed: Sep. 6, 1988

[51] Int. Cl.$^4$ .............................................. A61K 31/41
[52] U.S. Cl. ..................................................... 514/384
[58] Field of Search ......................................... 514/384

[56] References Cited

U.S. PATENT DOCUMENTS 4,775,688 10/1988 Kane et al. ........................... 514/384

OTHER PUBLICATIONS

Chemical Abstracts 107: 154339g (1987).
J. M. Kane: *Synthesis*(10), 912–14 (1987).
J. M. Kane, M. W. Dudley, S. M. Sorenson, and F. P. Miller: *J. Med. Chem.* 31(6), 1253–8 (1988).

Primary Examiner—Jerome D. Goldberg
Attorney, Agent, or Firm—Edlyn S. Simmons

[57] ABSTRACT

This invention relates to a novel method for the treatment of hemorrhagic and thrombotic thrombocytosis by means of administration of a 5-(4-chlorophenyl)-2,4-dimethyl-3H-1,2,4-triazole-3-thione.

16 Claims, No Drawings

TREATMENT OF THROMOBOCYTOSIS WITH 5-(4-CHLOROPHENYL)-2,4-DIEMTHYL-3H-1,2,4-TRIAZOLE-3-THIONE

FIELD OF THE INVENTION

This invention relates to a novel method for the treatment of thrombocytosis by means of administration of 5-(4-chlorophenyl)-2,4-dimethyl-3H-1,2,4-triazole-3-thione.

More specifically, this invention relates to the treatment of thrombocytosis and the prevention of thrombosis and hemorrhage resulting therefrom through administration of the compound of the formula

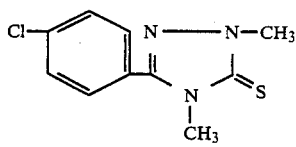

I and the tautomers thereof.

BACKGROUND OF THE INVENTION

Thrombocytosis is a condition in which there are an increased number of platelets in the peripheral blood. Thrombotic thrombocytosis, in which the increased platelet count results in intravascular clotting, is most commonly associated with chronic myeloproliferative diseases. Examples of myeloproliferative diseases include primary thrombocythemia, polycythemia vera and chronic myelogenous leukemia. Primary thrombocythemia, also known as essential thrombocythemia, idiopathic thrombocythemia, hemorrhagic thrombocythemia and megakaryocytic leukemia, may result in spontaneous hemorrhages, both external and into the tissues. Polycythemia vera involves both an increase in red cell mass and an increase in total blood volume. An increase in circulating platelets is also often associated with reactive processes. In reactive processes to splenectomy, surgery, inflammation, iron deficiency or hemorrhage, the platelets typically exceed one million per microliter. This level of thrombocytosis is accompanied by little tendency toward thrombosis unless there are additional risk factors such as preexisting arterial disease or prolonged immobility. In chronic myeloproliferative disease, circulating platelets often approach 5 million per microliter. In addition to hemorrhage, thrombosis is often observed in association with such a high number of platelets. It has been postulated that thrombosis is due to spontaneous platelet aggregation in the circulation of patients with chronic myeloproliferative disease. Left untreated, the thrombosis may lead to ischemic lesions of the toes, pulmonary embolism, apoplexy, and even death.

Current clinical practice in these neoplastic-thrombocytosis patients is to lower the platelet count when values exceed one million per microliter. The treatment of choice is presently concomitant platelet pheresis in association with marrow suppressive therapy using radioactive phosphorus or alkylating agents. The disadvantages to this concomitant therapeutic approach is that the former therapy requires hospitalization and technical assistance and the latter treatment is well recognized to enhance leukemogenic responses.

A more desirable pharmaceutical approach to this condition would be administration of a drug with a direct, specific effect on lowering the platelet population without any side effects. Currently, at least two drugs with the desired thrombocytopenic effect are being evaluated in the treatment of thrombocytosis associated with chronic myeloproliferative disease: hydroxyurea and anagrelide. In the case of hydroxyurea, granulocytopenia is an undesired side effect and there is also a theoretical concern that this drug may have leukemogenic potential. Anagrelide, 6,7-dichloro-1,5-dihydroimidazo-[2,1-b]quinazolin-2(3H)-one monohydrochloride, which is currently being given 4 times a day with maintenance doses of 1.5 to 4.0 mg/day, has been reasonably effective in lowering platelet counts beginning about 5 days after initiation of treatment. However, in addition to transient side effects of headache and nausea, higher doses of this drug may cause potent aggregation. U.S. Pat. No. 4,743,445, indicates that alpha interferon may be used to treat thrombocythemia, but that it also reduces the white blood cell count.

DETAILED DISCLOSURE OF THE INVENTION 5-(4-Chlorophenyl)-2,4-dimethyl-3H-1,2,4-triazole-3-thione has now been discovered to lower the platelet population in the blood without the toxic side effects of compounds previously shown to combat thrombocytosis. 5-(4-Chlorophenyl)-2,4-dimethyl-3H-1,2,4-triazole-3-thione has previously been found to slow antidepressant activity. The usefulness of this compound as an antidepressant and methods for its preparation are described in co-pending U.S. patent applications Ser. Nos. 51,101 and 51,103, now U.S. Pat. No. 4,775,688, filed May 15, 1987, and Ser. No. 87,018, filed Aug. 19, 1987, which are hereby incorporated by reference.

Studies of orally administered 5-(4-chlorophenyl)-2,4-dimethyl-3H-1,2,4-triazole-3-thione have demonstrated that a dose-related thrombocytopenia occurred after two weeks in rats at doses of 40–360 mg/kg/day and after one week in dogs at doses of 5–50 mg/kg/day. Further studies in dogs show that the thrombocytopenia begins to develop about 48 hours after the initiation of dosing, reaches its maximum level (10,000–40,000/cmm) after one week of treatment, and remains relatively unchanged after a second week of dosing. Megakaryocytes in the bone marrows of treated rats and dogs were comparable to those of control animals or were slightly increased, indicating that the drug did not cause abnormalities in platelet production. The drug-induced thrombocytopenia also does not appear to be the result of aggregation. Preliminary in vitro studies using dog platelets indicate that the drug does not cause aggregation and may also have potent anti-aggregating properties.

In the following table, platelet counts are compared in groups of two dogs, given various doses of 5-(4-chlorophenyl)-2,4-dimethyl-3H-1,2,4-triazole-3-thione orally for a period of two weeks. The platelet counts were compared with the pretest average for the tested dogs and for controls.

| Dose, mg/kg/day | Count × 1000/cmm pretest | Count × 1000/cmm after 1 week | Count × 1000/cmm after 2 weeks | % of Normal after 2 weeks |
|---|---|---|---|---|
| 0 | 484 | 497 | 381 | — |

REDUCTION IN PLATELET COUNT IN DOGS AFTER ORAL ADMINISTRATION OF 5-(4-CHLOROPHENYL)-2,4-DIMETHYL-3H—1,2,4-TRIAZOLE-3-THIONE -continued

| Dose, mg/kg/day | Count × 1000/cmm pretest | Count × 1000/cmm after 1 week | Count × 1000/cmm after 2 weeks | % of Normal after 2 weeks |
| --- | --- | --- | --- | --- |
| 5 | 416 | 317 | 297 | 70 |
| 10 | 585 | 223 | 248 | 50 |
| 20 | 419 | 129 | 161 | 30 |
| 30 | 421 | 24 | 42 | 10 |
| 50 | 384 | 18 | 33 | 10 |

5-(4-Chlorophenyl)-2,4-dimethyl-3H-1,2,4-triazole-3-thione is well absorbed, resulting in a significant concentration of the drug in plasma collected two and twenty-four hours after dosing. Thus the compound has a prolonged duration of activity following administration. The half life of the drug in the plasma is long enough so as to allow once a day oral adminiatration during the period leading to and maintaining a thrombocytopenic effect.

In general, the compounds may be expected to exert its thrombocytopenic effects at dose levels of about 0.25–50 mg/kg of body weight per day although, of course, the degree of severity of the disease state, age of the patient and other factors determined by the attending diagnostician will influence the exact course and dosage regimen suitable for each patient. In general, parenterally administered doses should be about ¼ to ½ that of the orally administered dose.

For oral administration, the compound can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compound can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration, the compound may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compound can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradeable polymers or synthetic silicones, for example Silastic ®, a silicone rubber manufactured by the Dow-Corning Corporation.

The compound is preferably administered orally as a single daily dose of from 0.25 to 30 mg/kg, with a dosage of from 5 to 25 mg/kg being more preferred.

EXAMPLE 1

2,4-Dimethylthiosemicarbazide

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) and sieve dry ethanol (30 ml). The reaction is exothermic and gently refluxes as the isothiocyanate is added. A precipitate soon forms. After stirring overnight, the reaction was cooled in an ice bath. The precipitate was then collected by filtration, washed with a little cold isopropanol, and dried by suction affording a pale yellow powder: 26.7 g (75%). This material was crystallized two times from water and two times from isopropanol affording small colorless needles: 14.7 g (41%), mp 135°–137° C.

EXAMPLE 2

1-(4-Chlorobenzoyl)-2,4-Dimethylthiosemicarbazide

To a stirred solution of 2,4-dimethylthiosemicarbazide (1.19 g, $1.00 \times 10^{-2}$ mole) and pyridine (10 ml) was added dropwise 4-chlorobenzoyl chloride (1.3 ml, $1.02 \times 10^{-2}$ mole). The reaction turns yellow and a mild exotherm is noted. After stirring overnight the reaction was evaporated to dryness affording a beige solid: 3.61 g (97%) which represents a mixture of the desired 1-(4-chlorobenzoyl)-2,4-dimethylthiosemicarbazide and pyridine hydrochloride. In general this mixture was used without further purification in the subsequent cyclization step. If pure 1-(4-chlorobenzoyl)-2,4-dimethylthiosemicarbazide is desired, the above mixture is treated with water and that which does not dissolve is collected by filtration. After drying by suction this material is crystallized from ethanol affording colorless matted needles: 1.03 g (40%), mp 206°–208° C. (decomp).

EXAMPLE 3

5-(4-Chlorophenyl)-2,4-Dimethyl-3H-1,2,4-Triazole-3-Thione

The 1:1 mixture of 1-(4-chlorobenzoyl)-2,4-dimethylthiosemicarbazide and pyridine hydrochloride (3.61 g of mixture) from Example 2 and 1 molar aqueous NaHCO$_3$ (100 ml, $1.00 \times 10^{-1}$ mole) were stirred and warmed to reflux. After refluxing for 5 hours the reaction was allowed to cool. It was then placed in a refrigerator for several hours before the precipitate was collected by filtration. The collected material was dried partially by suction before being transferred to a desiccator where it was dried at high vacuum. This affords the desired product as a beige powder: 2.01 g (84%). This was purified by flash chromatography and subsequent crystallization from isopropanol yielding small, slightly yellowish plates: 1.74.g (73%), mp 113°–115° C.

EXAMPLE 4

5-(4-Chlorophenyl)-2,4-Dimethyl-3H-1,2,4-Triazole-3-Thione

To a stirred, room temperature, solution of 5-(4-chlorophenyl)-2,4-dimethyl-3H-1,2,4-triazole-3-one (0.90 g, $4.0 \times 10^{-3}$ mole), bis(tricyclohexyltin) sulfide (4.63 g, $6.02 \times 10^{-3}$ mole) and sieve dry toluene (63 ml), was added via syringe a methylene chloride solution of BCl$_3$ (4.1 ml, 4.1×10$^{-3}$ mole) The reaction was then heated to reflux. After refluxing overnight, the entire reaction mixture was transferred to a 500 ml round bottom flask and the toluene was evaporated at reduced pressure. The solid concentrate was slurried with Et$_2$O (250 ml) and 10% aqueous KF (100 ml) was added. The flask was stoppered and the two phases shaken. This results in the formation of a colorless solid, presumably (C$_6$H$_{11}$)$_3$SnF, which was removed by filtration. The filtrate was transferred to a separatory funnel and the aqueous KF layer was separated. The ethereal layer was washed with sat. aqueous NaCl (100 ml) before being dried over anhydrous Na$_2$SO$_4$. The drying agent was removed by filtration and the filtrate was evaporated at reduced pressure leaving a yellowish oil which solidified to a pale yellow solid: 2.0 g. The oil was flash chromatographed with 2% EtOAc/CH$_2$Cl$_2$ affording a colorless (faintly yellowish) solid: 0.71 g. The solid is crystallized from isopropanol to yield the desired product as colorless plates: 0.68 g (71%) mp 114°–116° C.

I claim:

1. A method for the treatment of thrombocytosis which comprises administration to a patient suffering from a myeloproliferative disease of an amount effective to lower the platelet count of 5-(4-chlorophenyl)-2,4-dimethyl-3H-1,2,4-triazole-3-thione or a tautomer thereof.

2. A method according to claim 1 wherein the myeloproliferative disease is essential thrombocythemia.

3. A method according to claim 1 wherein the myeloproliferative disease is polycythemia vera.

4. A method according to claim 1 wherein the myeloproliferative disease is chronic myelogenous leukemia.

5. A method according to claim 1 wherein 5-(4-chlorophenyl)-2,4-dimethyl-3H-1,2,4-triazole-3-thione is administered at a dosage of from 0.25 to 50 mg/kg/day.

6. A method according to claim 5 wherein 5-(4-chlorophenyl)-2,4-dimethyl-3H-1,2,4-triazole-3-thione is administered at a dosage of from 5 to 25 mg/kg/day.

7. A method according to claim 1 wherein 5-(4-chlorophenyl)-2,4-dimethyl-3H-1,2,4-triazole-3-thione is adminstered orally.

8. A method according to claim 7 wherein 5-(4-chlorophenyl)-2,4-dimethyl-3H-1,2,4-triazole-3-thione is administered as a single daily dose.

9. A method for the prevention of hemorrhage and thrombosis in a patient suffering from a myeloproliferative disease and having an elevated platelet count which comprises administration of an amount effective to lower the platelet count of 5-(4-chlorophenyl)-2,4-dimethyl-3H-1,2,4-triazole-3-thione or a tautomer thereof.

10. A method according to claim 9 wherein the myeloproliferative disease is essential thrombocythemia.

11. A method according to claim 9 wherein the myeloproliferative disease is polycythemia vera.

12. A method according to claim 9 wherein the myeloproliferative disease is chronic myelogenous leukemia.

13. A method according to claim 9 wherein 5-(4-chlorophenyl)-2,4-dimethyl-3H-1,2,4-triazole-3-thione is administered at a dosage of from 0.25 to 50 mg/kg/day.

14. A method according to claim 13 wherein 5-(4-chlorophenyl)-2,4-dimethyl-3H-1,2,4-triazole-3-thione is administered at a dosage of from 5 to 25 mg/kg/day.

15. A method according to claim 9 wherein 5-(4-chlorophenyl)-2,4-dimethyl-3H-1,2,4-triazole-3-thione is administered orally.

16. A method according to claim 15 wherein 5-(4-chlorophenyl)-2,4-dimethyl-3H-1,2,4-triazole-3-thione is administered as a single daily dose.

* * * * *